United States Patent [19]
Jeanson et al.

[11] Patent Number: 5,360,429
[45] Date of Patent: Nov. 1, 1994

[54] DEVICE FOR STRAIGHTENING, FIXING, COMPRESSING, AND ELONGATING CERVICAL VERTEBRAE

[75] Inventors: Jean-François Jeanson, Assenay; Jean Huppert, Saint Etienne; Alex Autrique, Pau; Joël Remond, Lyons; Francis Lesoin, Lille, all of France

[73] Assignee: JBS Societe Anonyme, France

[21] Appl. No.: 19,547

[22] Filed: Feb. 19, 1993

[30] Foreign Application Priority Data

Feb. 20, 1992 [FR] France .................. 92 01913
Sep. 11, 1992 [FR] France .................. 92 10836

[51] Int. Cl.5 ............................. A61B 17/58
[52] U.S. Cl. ..................................... 606/61
[58] Field of Search ............. 606/61, 60, 62, 69

[56] References Cited

U.S. PATENT DOCUMENTS

| | | | |
|---|---|---|---|
| 5,007,909 | 4/1991 | Rogozinski | 606/61 |
| 5,116,334 | 5/1992 | Cozad et al. | 606/61 |
| 5,133,716 | 7/1992 | Plaza | 606/60 |

FOREIGN PATENT DOCUMENTS

| | | |
|---|---|---|
| 0301489 | 7/1988 | European Pat. Off. . |
| 0308156 | 9/1988 | European Pat. Off. . |
| 2615095 | 5/1987 | France . |
| 2650173 | 7/1989 | France . |
| 9115453 | 12/1991 | France . |
| 3916198 | 11/1990 | Germany .................. 606/61 |
| 9101691 | 7/1990 | WIPO . |

Primary Examiner—Tamara L. Graysay
Attorney, Agent, or Firm—Harrison & Egbert

[57] ABSTRACT

The present invention is a device for the straightening, fixing, compressing, and elongating of cervical vertebrae. The present invention includes a pair of rods extending to occipital plates. The occipital plates conform to the shape and inclination of the occiput. A connecting plate is attached to the ends of the occipital plates. A pedicular clamp having hooks is attached on one of the rods. A hook is connected to another of the rods. Screws are provided so as to secure the occipital plates and the connecting plate to the occiput and the connecting plate to ends of the occipital plates.

5 Claims, 4 Drawing Sheets

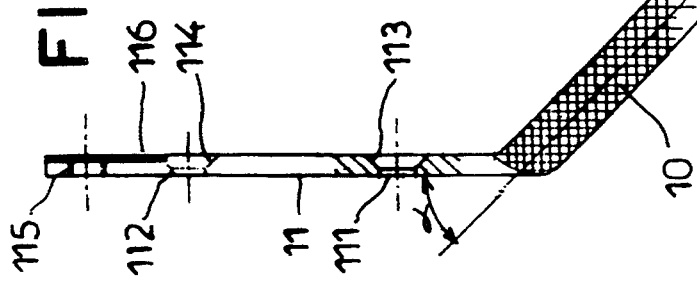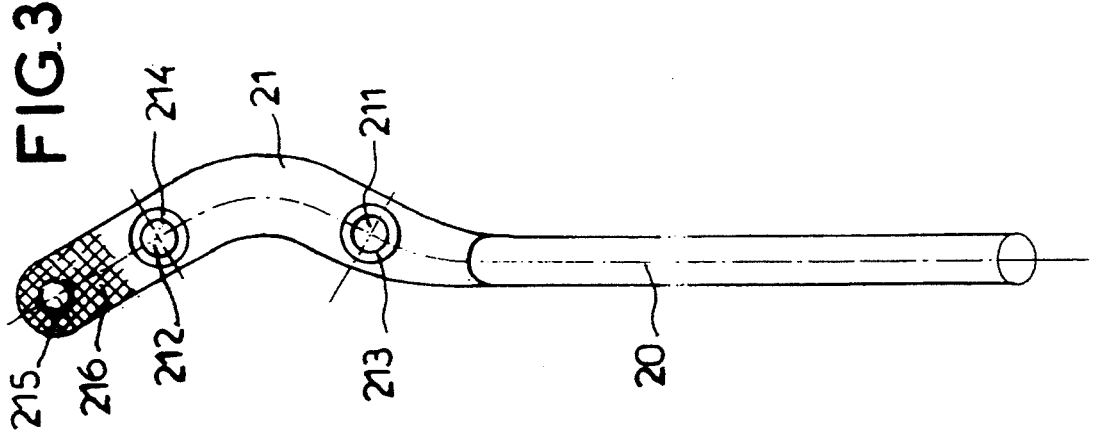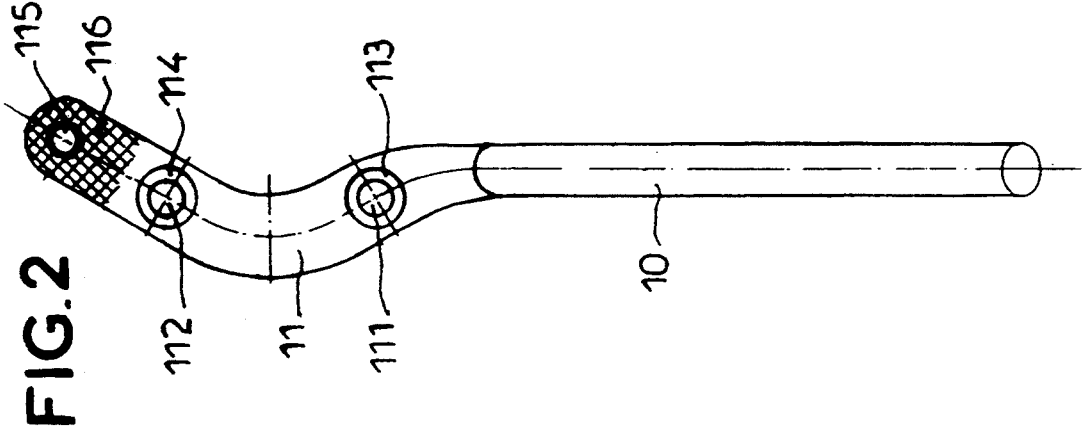

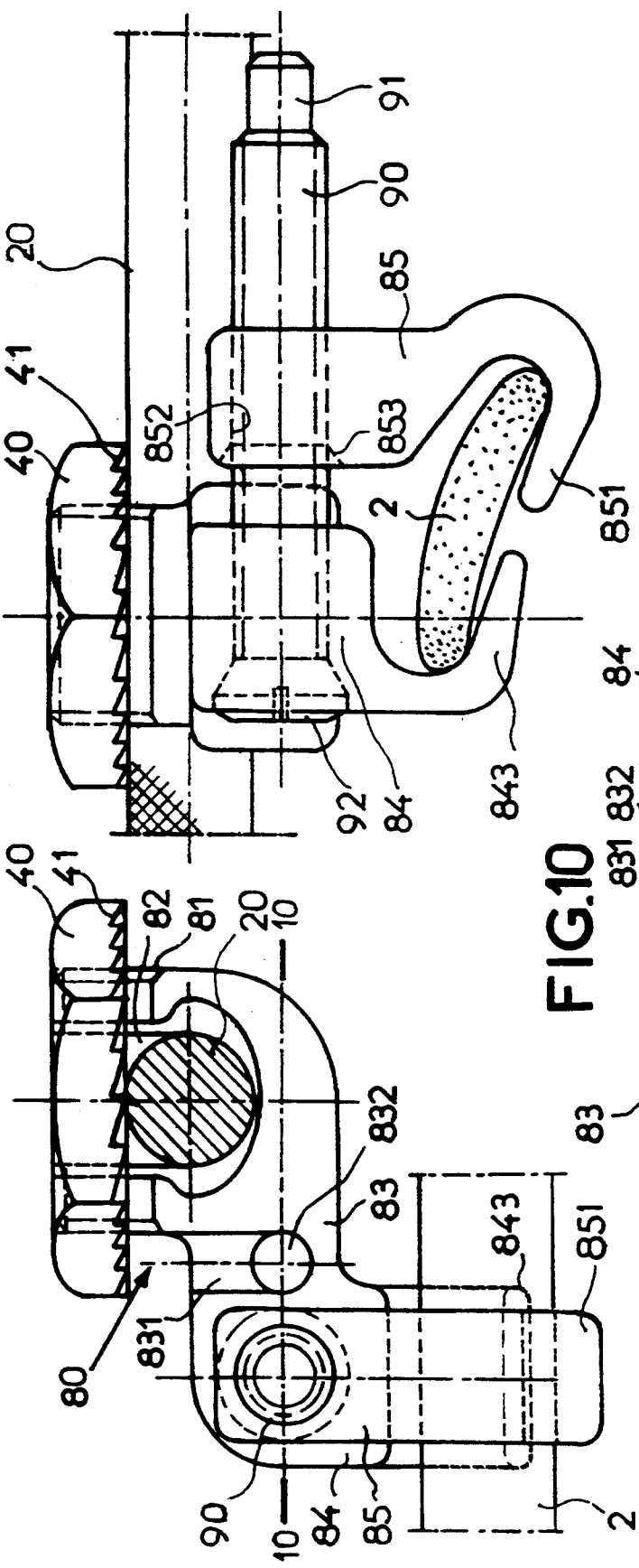

DEVICE FOR STRAIGHTENING, FIXING, COMPRESSING, AND ELONGATING CERVICAL VERTEBRAE

TECHNICAL FIELD

The invention concerns a straightening, fixation, compression and elongation device for cervical vertebrae.

BACKGROUND ART

Several rachidian straightening and stretching devices are already known of, such as those described in French patent applications No. 89 10176 and 91 15455.

Such devices use implants with screws and hooks on which the head features longitudinal grooves at the bottom of which connecting and staying rods, usually milled or fluted on the outside, are locked. The locking of said rods inside the grooves results from the deformation of the groove sides brought together through a cylindrical screw system achieved around the head of the implants and hooks and a tapered bolt which, when tightened, gradually brings together the groove sides and thus causes partial crimping of the rod inside the grooves and the gripping of the rod against the bottom of said grooves through the base of a nut notched to resist any inadvertent unscrewing; various means of longitudinal and lateral connection being provided for.

The purpose of the device under the invention is to permit the straightening, fixation and compression or elongation of the cervical vertebrae, alone or in addition to the rachidian vertebrae, while providing for some lateral offsetting of the bottom clamps in relation to the top clamps in order to take into account some shape differences in the concerned vertebrae, or to maintain a specific alignment with the rods which might already be used on the same patient for rachidian straightening and stretching.

As a matter of fact, regardless of the scoliosis problems which apply to all rachis vertebrae, it happens very often that the cervical vertebrae are accidentally injured, especially upon brutal falls.

SUMMARY OF THE INVENTION

The device under the invention is mainly characterized by the fact that it basically consists of two rods, each extended at one end by a perforated occipital plate, taking the shape and inclination of the occiput, of a connecting plate, of at least one clamp and one hook, and of screws designed to fasten into the occiput after running through the holes drilled for that purpose in the occipital plates.

Under a preferred embodiment, the occipital plates extending one end of each rod, form lengthwise a 45° angle in relation to each rod and sideways a V with uneven branches, open to the outside at a 120° angle; both branches being connected through a 10 mm inside radius round at an angle of approx. 60°.

The holes drilled in each occipital plate are made of two chamfered, superimposed cylindrical holes and of a threaded hole located at the top end, designed to receive, if needed, the screw for fastening to the occipital connecting plate.

The connecting plate features in its middle a chamfered cylindrical hole designed to receive a screw for fastening to the occiput, and two chamfered grooves, arranged symmetrically in relation to the hole, and allowing for passage of the milled-head screws used to fasten said connecting plate onto the end of the occipital plates connected to the rods; the chamfers of the grooves and of the cylindrical hole being located on the same side of the plate.

Preferably, the side of the connecting plate, opposite to the chamfers of the grooves and main fastening cylindrical hole, is milled or fluted, as well as the end of the occipital plates, on the side against which the connecting plate rests.

Under a simplified mounting arrangement of the device, the occipital plates can be attached directly onto the occiput without a connecting plate, after having been brought together through mere rotation of the respective rod in relation to the device fastening said rod to the vertebrae.

The rods are connected to the vertebrae through auto-stable clamps designed to be mounted on a rod through a grooved cylindrical head, threaded on the outside, into which a tapered nut can be screwed, and on a vertebra lamina through two hooks with an inclined base connected with a screw, with one of those hooks being integral part of the grooved cylindrical head used for fastening to the rod. The nose of each hook is respectively open at an angle of approx. 20° with respect to the hook integral with the grooved cylindrical head, and closed at the same angle for the mobile hook so as to fit the lateral inclination of the laminae of the cervical vertebrae.

Preferably, the hooks are offset laterally in relation to the groove on the grooved and threaded cylindrical head, and the arm connecting said grooved and threaded cylindrical head to the hook integral therewith features two symmetrical impressions reproducing the shape of the noses of a catch-type gripping clamp; the threaded cylindrical head and hooks being respectively located on either side of the gripping impressions without overlapping them.

Under a special embodiment of the clamp under the invention, the gripping impressions each consist of a groove taking the shape of the noses of the gripping clamp, delimited lengthwise by a cylindrical cavity taking the shape of the catches of said gripping clamp.

The screw connecting both hooks features, at the end of its threaded section, an aligning and centering teat whose penetration inside the mobile hook threaded hole is facilitated by a chamfer.

The advantages resulting from this invention lie mainly in the fact that the device is suitable for all individual cases and morphologies because of the adjustable spacing of the occipital plates, on one hand, and of the presence of hooks on the holding-down and locking clamp, on the other hand; more especially as the straightening, fixation, elongation or compression of the vertebrae can be achieved using the instruments and tools designed for the application of the rachis stretching devices described in French patent applications No. 89 10178 and 91 15453 without any hindrance with respect to the use of such tools.

BRIEF DESCRIPTION OF THE DRAWINGS

Other features and advantages shall become evident in the following description of an embodiment of the cervical device, executed according to the invention and given as a non-limiting example, based on the attached drawings where:

FIG. 2 represents a top view of the left component,
FIG. 3 represents a top view of the right component,
FIG. 4 represents a side view of either component, in a partial cross-section,
FIG. 8 represents a front view of the clamp,
FIG. 9 represents a side view of the clamp according to FIG. 8,
FIG. 10 represents a bottom sectional view along 10—10 of the clamp according to FIG. 8.

DETAILED DESCRIPTION OF THE INVENTION

Figure 1:
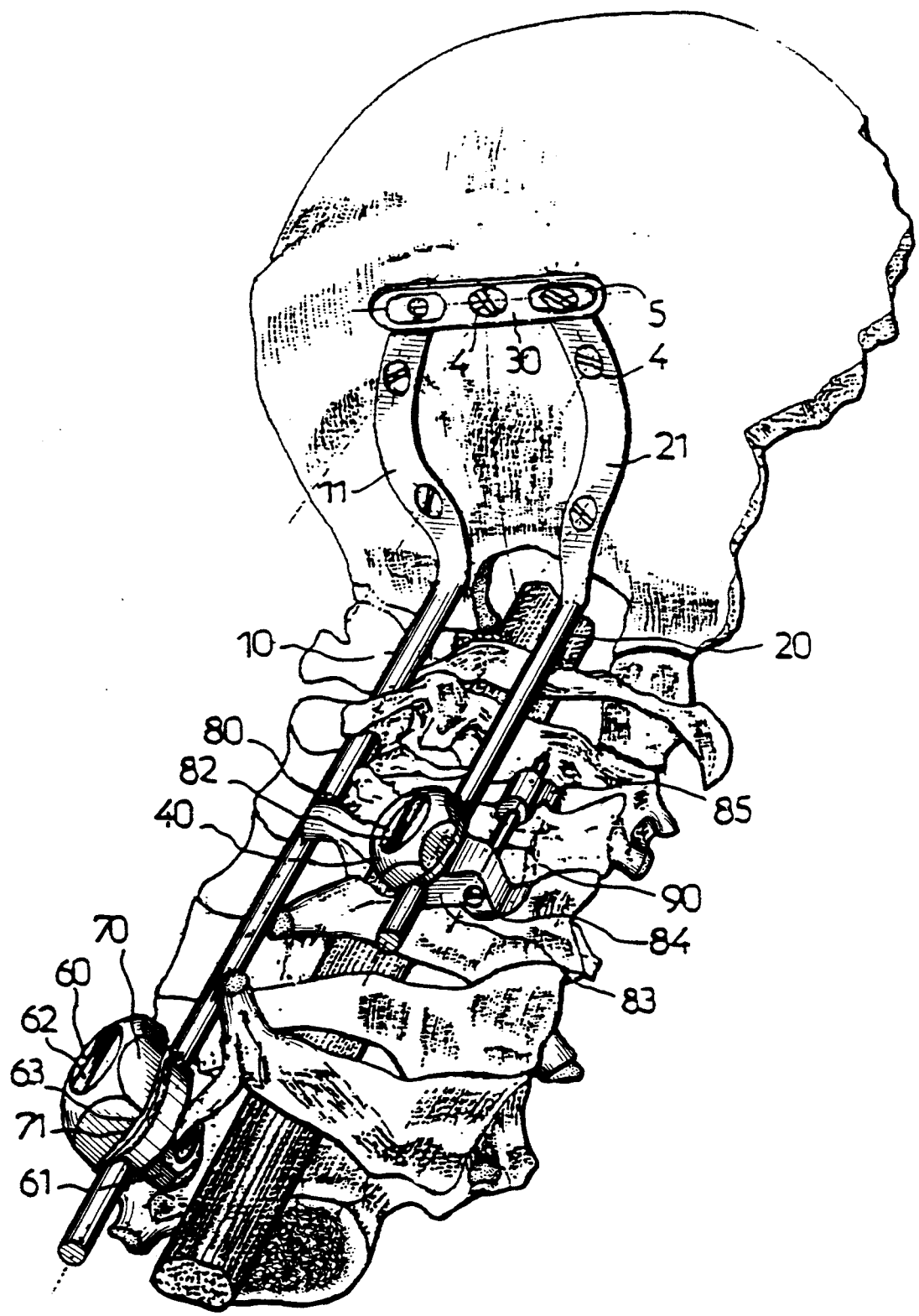
FIG. 1 represents a view in perspective of the device in place on a patient.

The figures represent a cervical vertebrae straightening, fixation, compression and elongation device under the invention, consisting of two milled rods 10 and 20, extended at the top through occipital plates 11 and 21, featuring respectively two smooth openings 111, 112, with chamfers 113, 114, a threaded opening 115 and a fluted section 116, and two smooth openings 211, 212, with chamfers 213, 214, a threaded opening 215 and a fluted section 216, connected at their end through a connecting plate 30, featuring groove 31 with chamfer 311, featuring symmetrical groves 32 and 33 with chamfers 321, 331, and milled side 34; plates 11, 21 and 30 being fastened to the occiput through screw 4, and connecting plate 30 to occipital plates 11, 21 through screw 5; one of rods 10 being fastened to the vertebrae through hook 61 located below a cylindrical head 60, with groove 62, with outside thread 63, onto which nut 70 with tapered thread and notched base 71 is screwed; the other rod 20 being fastened to the vertebrae through a clamp consisting of a cylindrical head 80 with groove 82 and outside thread 81, onto which a nut 40 with locking notches 41 is screwed; a fixed hook 84, is connected to cylindrical head 80 through arm 83 comprising laterally impressions each made of a groove 831 or 833 limited by a cavity 832 or 834; and of a mobile hook 85, connected to fixed hook 84 through screw 90, with an alignment teat 91 and milled head 92, mounted in hole 841 with milled opening 842 of hook 84 and screwing into a threaded hole 852 with inlet chamfer 853 provided for in hook 85. The nose 843 of fixed hook 84 and the nose 851 of mobile hook 85 are respectively open and closed at an angle of approx. 20° given as a non limiting example.

Figure 5:
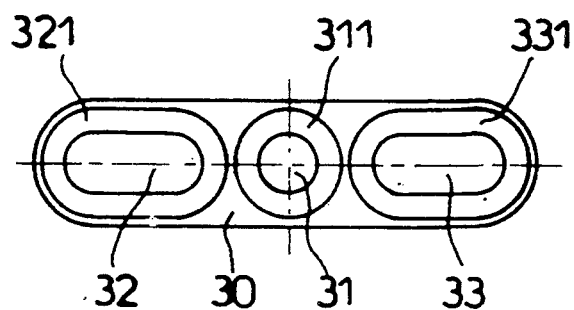
FIG. 5 represents a top view of the connecting plate.
Figure 6:
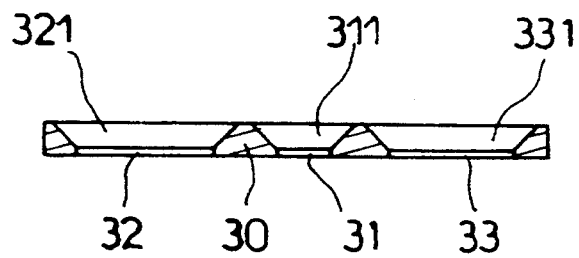
FIG. 6 represents a side view of the connecting plate, along a lengthwise section.
Figure 7:
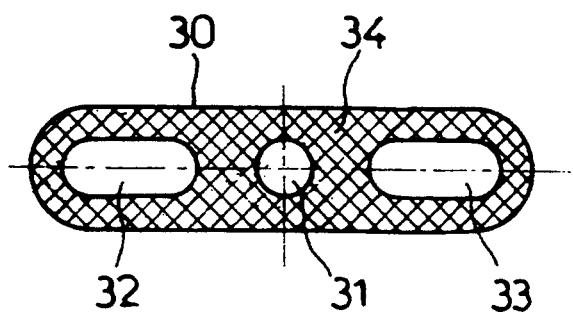
FIG. 7 represents a bottom view of the connecting plate.

Upon closer examination of FIGS. 1 through 7, it can be noted that the occipital plates 11 and 21 extend outwardly of rods 10 and 20 and are connected by screw 4. The ends of the occipital plates 11 and 21 are joined by screws 5 to the connecting plate 30. The respective fluted sections 116 and 216 and milled side 34 are placed against each other. Screw 4 is used to screw the connecting plate 30 against the occiput. Rods 10 and 20 are inserted, respectively, into grooves 62 and 82 of cylindrical heads 60 and 80 of hooks 61 and 84. The rods are locked in the bottom of the grooves with nuts 70 and 40 using instruments described in French patent applications 8910178 and 9115453. As a result, it is possible to achieve the straightening, fixation, compression or elongation of the cervical vertebrae using, as needed, one or more of the single hooks 61 or the clamps with hooks 84 and 85. As already mentioned above, connecting plate 30 can in some cases be eliminated in favor of the ends of occipital plates 11 and 21 being brought together for direct attachment of said ends onto the occiput using for that purpose openings 115 and 215.

Upon closer examination of FIGS. 8 through 10, it can be seen that the clamps 84 and 85 can be mounted on a connecting rod 20 so as to clamp onto a lamina 2; then, in the order chosen, one need only to present, for example, tapered nut 40 on the end of the threaded section 81 of cylindrical head 80, imprisoning connecting rod 20 inside head groove 82, then to keep tightening tapered nut 40 until cylindrical head 80 is crimped on rod 20 and at the same time nut 40 is locked on the milled section of rod 20 through notches 41 using for that purpose a special wrench and holding tool, as described in patent application No. 91 15453; this operation being followed by a tightening of hooks 84 and 85 of the clamp around lamina 2 through a rotating action on screw 90 using a wrench or screwdriver with a tip suitable for the existing impression in head 92 of screw 90.

Another method can be to first screw the connecting rods onto the occiput, to mount the clamps on the concerned pediculus without locking them so as to allow for lateral sliding, if needed, when matching threaded and grooved cylindrical head 80 with rod 20 upon the straightening, fixation, compression or elongation of the concerned cervical vertebrae; the clamps can then be locked on the respective rod 20 and noses 843 and 851 of hooks 84 and 85 can be tightened on lamina 2.

It is understood that depending on whether the clamp is mounted on the left rod 10 or right rod 20, a proper clamp shall be used on which the fixed hook 84 shall have its nose 843 pointing to the right or to the left of its arm 83; the mobile hook 85 remaining unchanged.

The device under the invention, although designed to be used mainly in human surgery, can also be used for animal surgery, especially on dogs for cervical applications, and also for lumbar surgery with or without adjustment.

We claim:
1. A cervical vertebrae straightening, fixation, compression and elongation device comprising:
   a first rod and a second rod;
   an occipital plate means extending from said first rod, occipital plate means for conforming to a shape and inclination of an occiput;
   a connecting plate attached by a fastener to an end of said occipital plate means;
   at least one clamp attached to one of said first and second rods, said clamp having a hook formed thereon;
   a hook member attached to the other of said first and second rods; and
   a screw means received by said occipital plate means, and screw means for attaching said occipital plate means to the occiput.
2. The device according to claim 1, said occipital plate means comprising a first occipital plate and a second occipital plate extending at a 45° angle relative to said rods, said occipital plates extending in a generally V-shaped configuration both branches of the V-shaped configuration being connected through a 10 mm inside radius at an angle of approximately 60°.
3. The device according to claim 1, said screw means comprising two screws.
4. The device according to claim 1, said connecting plate having a chamferred cylindrical hole in a middle of said connecting plate, said connecting plate having chamferred grooves at opposite ends thereof.
5. The device according to claim 4, said connecting plate having a milled surface, said chamferred cylindrical hole having a chamfer opposite said milled surface.

* * * * *